(12) United States Patent
McGhan

(10) Patent No.: US 6,733,512 B2
(45) Date of Patent: May 11, 2004

(54) SELF-DEFLATING INTRAGASTRIC BALLOON

(76) Inventor: Jim J. McGhan, 1865 Meiners Rd., Ojai, CA (US) 93023

( * ) Notice: Subject to any disclaimer, the term of this patent is extended or adjusted under 35 U.S.C. 154(b) by 197 days.

(21) Appl. No.: 10/094,244

(22) Filed: Mar. 7, 2002

(65) Prior Publication Data
US 2003/0171768 A1 Sep. 11, 2003

(51) Int. Cl.$^7$ .............................................. A61M 29/00
(52) U.S. Cl. ................................... 606/192; 604/99.02
(58) Field of Search ............................... 606/192–198, 606/191, 199, 151, 157; 604/96.01, 97.01, 99.01, 99.02, 99.03

(56) References Cited

U.S. PATENT DOCUMENTS

| | | | | |
|---|---|---|---|---|
| 5,370,618 A | * | 12/1994 | Leonhardt | 604/192 |
| 6,454,785 B2 | * | 9/2002 | De Hoyos Garza | 606/192 |
| 6,579,301 B1 | * | 6/2003 | Bales et al. | 606/192 |

* cited by examiner

Primary Examiner—Kevin T. Truong
(74) Attorney, Agent, or Firm—Michael G. Petit

(57) ABSTRACT

An intragastric balloon device adapted to be inserted into the stomach for treating obesity in humans by reducing the stomach volume. The intragastric balloon device includes a flexible, inflatable balloon having an interior chamber defining a volume. A portion of the balloon has a self-sealing valve thereon to facilitate the introduction of an insufflation catheter into the interior chamber and to facilitate sealing of the catheter track upon removal of the insufflation catheter. The volume of the interior chamber, and the volume occupied by the balloon within the stomach of a patient, is adjusted by injecting an inflation fluid into the balloon's interior chamber. The balloon further includes a deflation valve in a portion thereof. The deflation valve is a patch that has a bioabsorbable or biodegradable portion. The patch forms a portion of the wall of the balloon and is in leakproof engagement therewith. After the balloon has resided within the stomach for a predetermined period of time, the deflation valve becomes leaky due to disintegration of the bioabsorbable or biodegradable material and the balloon deflates within the stomach, thereafter to be passed through the patient's digestive tract and excreted. The residence time of the balloon within the stomach depends upon the choice of biodegradable material incorporated into the patch and the construction of the deflation valve.

4 Claims, 2 Drawing Sheets

SELF-DEFLATING INTRAGASTRIC BALLOON

BACKGROUND OF THE INVENTION

1. Field of the Invention

The present invention is in the field of implantable weight control devices. More particularly, the present invention is directed to an intragastric balloon which has certain improved features enabling the balloon to be removed from the stomach noninvasively after a predetermined period of time has elapsed.

2. Prior Art

Gastric balloons used for achieving loss of weight in extremely obese persons have been known in the prior art. All gastric balloons utilized for this purpose function on the principle that an empty bag or balloon is placed into the stomach through the esophagus. Thereafter, the bag or balloon is filled (fully or partially) with a suitable insufflation fluid, such as saline solution, through a filler tube or catheter which is inserted into the stomach through the mouth or the nose. The balloon occupies space in the stomach thereby leaving less room available for food and creating a feeling of satiety for the obese person. Clinical experience of the prior art has shown that for many obese patients the intragastric balloons significantly help to control appetite and accomplish weight loss. Among the intragastric bags or balloons described in the prior art, one type remains connected to a filler tube during the entire time period while the balloon is in the stomach. The tube is introduced into the patient's stomach through the nostrils. Such an intragastric balloon is described, for example, in U.S. Pat. No. 4,133,315.

A second type of intragastric balloon of the prior art is placed into the stomach with the assistance of an appropriate catheter having a removable, relatively rigid stylette disposed in the central lumen thereof. After deployment of the balloon within the stomach, the stylette is removed from the catheter and the balloon is filled with saline, whereafter the catheter is withdrawn from the balloon and the stomach. An intragastric balloon of the second type is described, for example, in UK Patent Application GB 2 090 747. The balloon of this UK patent reference, like many intragastric balloons of the prior art, is substantially spherical in configuration. It is necessary for such prior art balloons to become deflated through a deflation tube before the empty balloon may be removed from the stomach either by retraction through the esophagus, or by allowing the deflated balloon to pass through the digestive system.

To accomplish the foregoing, intragastric balloons of the second type are normally equipped with a self-sealing valve into which the filler tube can be inserted. One difficulty frequently encountered in the prior art is related to finding the valve when the balloon is already in the stomach and the surgeon is attempting to reinsert the filler tube for the purpose of adding or removing fluid from the balloon. Those experienced in the art will readily appreciate that a small endoscopic light which can be lowered into the stomach for the procedure causes the surface of the balloon to shine in such a manner that visually locating the valve is rather difficult and the process of searching for the valve undesirably prolongs the surgical procedure. Moreover, even after the filler valve has been visually located, it is often still difficult or awkward for the surgeon to reinsert the tube into the filler valve. This is because the balloon is slippery and positionally unstable. In other words, the usually spherical (or substantially spherical) intragastric balloons readily rotate in the stomach, so that even a slight disturbance of the balloon may place the filler valve into virtually any possible position relative to the filler tube poised to engage it.

Gau et al., in U.S. Pat. No. 5,084,061, discloses an intragastric balloon having an ellipsoid or like configuration so that the balloon implanted in the stomach tends to rotate or rock only about one axis when a surgeon attempts to manipulate the balloon, for example, for the purpose of finding a filler valve and inserting a filler tube into it. For easy location, the filler valve is disposed on the equator. A retrieval tab is mounted to the exterior of the balloon, to permit capturing of the balloon and retrieval from the stomach, after the balloon has been deflated and is no longer desired for weight control purposes. Visual and X-ray opaque markers are located in the proximity of the valve and of the retrieval tab to facilitate their visualization with an endoscopic light when the balloon is in the stomach. Although the device includes means adapted to facilitate removal of the balloon from the stomach after the balloon has performed its intended function, such removal requires an invasive intubation in order to deflate the balloon.

For further and detailed information regarding intragastric balloons and related inflatable bags or the like designed for implantation into the human body, reference is made to the following patents and/or patent applications: U.S. Pat. Nos. 4,416,267; 4,485,805; 4,311,146; 4,236,521; 2,470,665; 3,046,988; 157,343; Published PCT Application No. PCT/US79/00354, and UK Patent Specification No. 1333096. The following articles or publications are also of interest: "Intragastral applizierter Ballon zur Behandlung der Adipositas", Deutsche Medizinische Wochenschrift (DMW), 1983, No. 8, page 315; "Intragastraler Appetitdepressor", Balloon Munch. Med. Wochenschrift 124 (1982), No. 2, page 39; "Der Magenballon in der behandlung der Adipositas permagna", Deutsche Medizinische Wochenschrift, 1984 No. 31/32, page 1200; "Intragastrick ballon som adipositasbehandling", UGESKY. LEGER 144/6, February 1982, page 394; and the article by Joanne Richard titled: "Gastric bubble battles bulge". In light of the above-noted and other shortcomings of the prior art, there is a need in the art for an intragastric balloon which can be deployed and inflated within the stomach and can be noninvasively removed from a patient's stomach after a predetermined period of time has elapsed. The present invention provides such an intragastric balloon.

SUMMARY

It is a primary object of the invention to provide an inflatable intragastric balloon device that may be invasively deployed within the stomach of a patient, inflated and noninvasively removed from within the stomach after a predetermined period of time has elapsed.

The present invention provides an intragastric balloon that includes a deflation valve in a portion thereof. The deflation valve is a patch that has a bioabsorbable or biodegradable portion. The patch forms a portion of the wall of the inflatable intragastric balloon and is in leakproof engagement therewith. After the balloon has resided within the stomach for a predetermined period of time, the deflation valve becomes leaky due to disintegration of the bioabsorbable or biodegradable material comprising the patch and the balloon deflates within the stomach, thereafter to be passed through the patient's digestive tract and excreted. The residence time of the balloon within the stomach depends upon the choice of biodegradable material incorporated into the patch and the detailed construction of the deflation valve.

DESCRIPTION OF THE PREFERRED EMBODIMENTS

Figure 1:
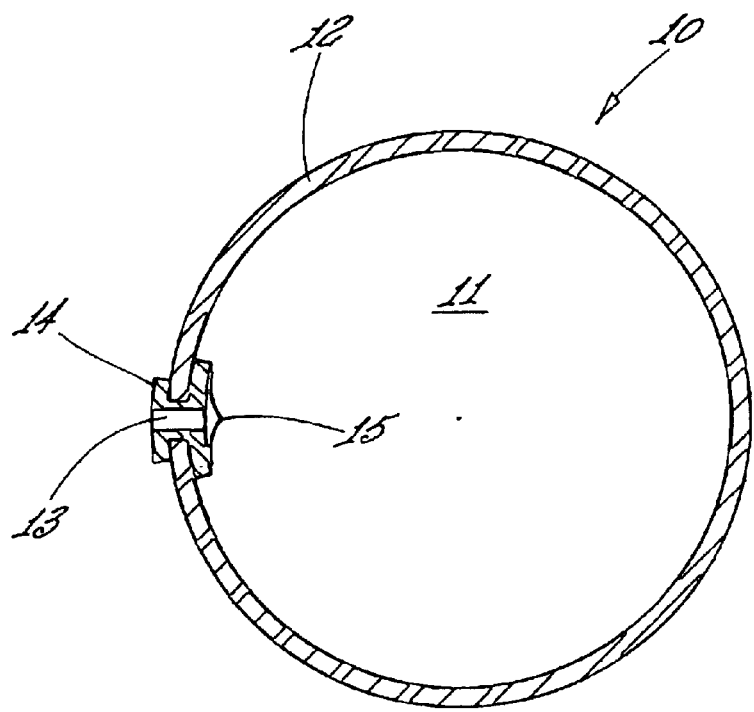
FIG. 1 is a cross-sectional view of an intragastric balloon for treating morbid obesity in accordance with the prior art.

A more or less "typical" intragastric balloon in accordance with the prior art is illustrated in transverse cross-sectional view at numeral 10 in FIG. 1. The intragastric balloon 10 comprises an interior chamber 11 enclosed by an inflatable shell 12. The shell 12, which usually comprises a biocompatible elastomer such as silicone rubber, has an opening 13 therein which is covered by an inflation valve 14 affixed to the shell 12 to form a leakproof seal therewith. The inflation valve 14 has a passageway 15 therethrough through which an insufflation (or deflation) catheter (not shown) may be introduced into the interior chamber 11 of the balloon 10 for injecting (or removing) an insufflation fluid into the interior chamber 11. In operation, the distal end of an insufflation catheter is inserted through the insufflation valve 14 into the interior chamber of the intragastric balloon 10. The (deflated) prior art balloon 10 is then introduced into the stomach transesohagaelly with the assistance of a rigid stylette inserted into the catheter's lumen. The stylus is then removed from the catheter and the balloon 10 is inflated by the injection of an insufflation fluid, normally saline, into the interior chamber via the catheter. When inflation is complete, the catheter is removed from the balloon and the track of the catheter is sealed by the insufflation valve 14. After implantation, the prior art device 10 must be deflated in order to be removed from the stomach. All prior art intragastric balloon devices require the invasive introduction of deflating means into the stomach in order to deflate the balloon in preparation for removing the balloon from the stomach. If the deflation catheter must be introduced into the interior chamber via the insufflation valve, an endoscope must be used.

Figure 2:
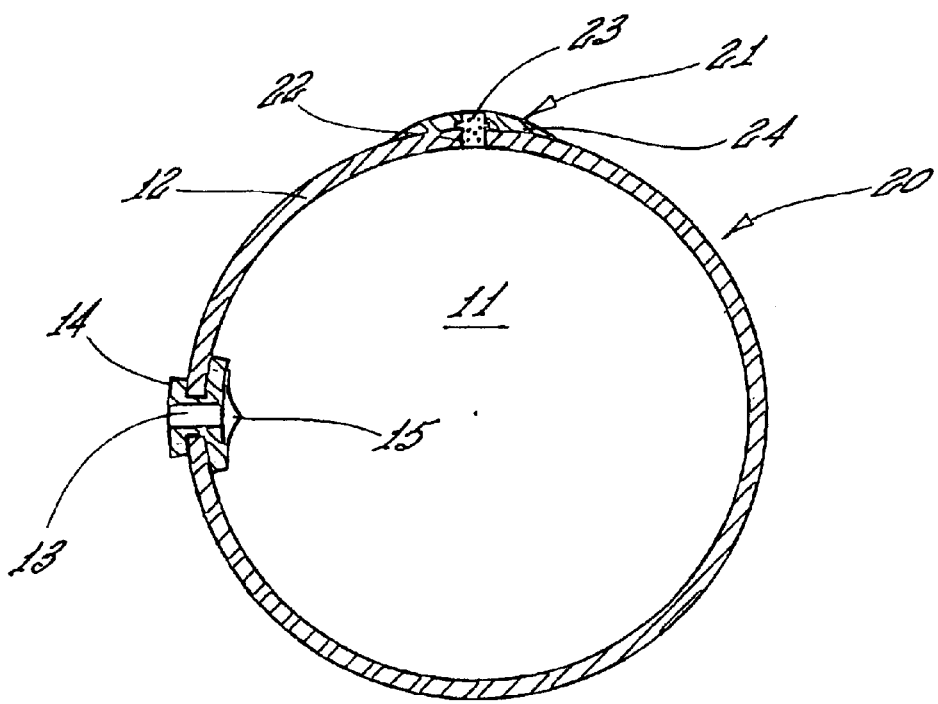
FIG. 2 is a cross-sectional view of an intragastric balloon for treating morbid obesity in accordance with a preferred embodiment of the present invention.
Figure 3:
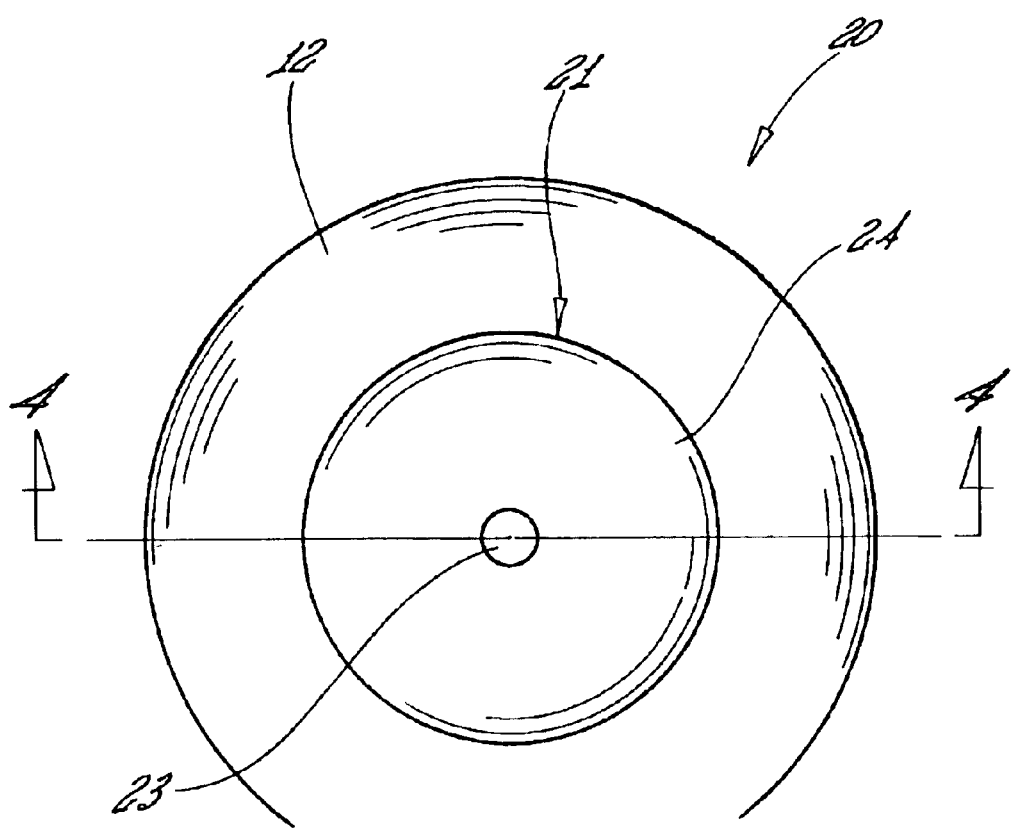
FIG. 3 is a top view of a deflation valve affixed to an elastomeric shell, a portion of which is illustrated, in accordance with the present invention.

Turning now to FIG. 2, an improved, self-deflating intragastric balloon 20 in accordance with the present invention is illustrated in transverse cross-sectional view. The intragastric balloon 20 is similar in construction to the prior art balloons 10, but includes a deflation valve 21 affixed to the shell 12 to overlie a hole 22 in the shell. The deflation valve 21 includes a biodegradable plug 23 supported by an elastomeric patch 24 made from a biocompatible material such as silicone rubber. In the event that the patch 24 material is uncured silicone elastomer, the patch 24 may be affixed to the silicone rubber shell 12 by vulcanization thereby providing a leakproof seal over the hole 22 in the shell 12. Following implantation of the balloon 20 within the stomach, digestive fluids slowly biodegrade the biodegradable plug 23 until the plug 23 disintegrates and the insufflation fluid within the interior cavity drains into the stomach thereby collapsing the balloon. The collapsed balloon will then pass through the pyloric valve into the duodenum and intestinal tract for excretion.

Figure 4:
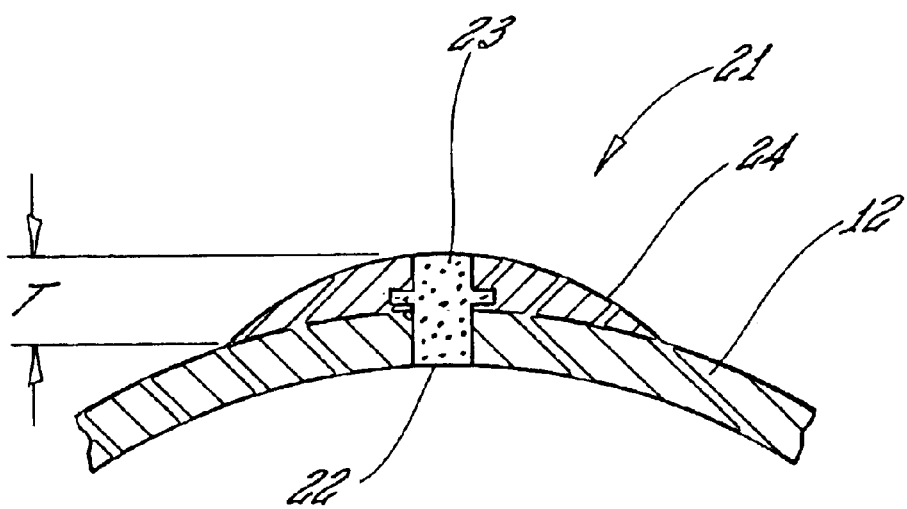
FIG. 4 is a side cross-sectional view of the deflation valve of FIGS. 2 and 3 taken along section line 4—4 of FIG. 3.

The residence time of the balloon 20 within the patient's stomach can be controlled by the choice of material used to fabricate the biodegradable plug 23 and the thickness T (FIG. 4) of the plug 23. Suitable biodegradable materials for fabricating the plug 23 include polymers or copolymers of lactide, glycolide, caprolactone, polydioxanone, trimethylene carbonate, polyorthoesters and polyethylene oxide, collagen, high molecular weight polysaccharides from connective tissue such as chondroitin salts. Other polysaccharides may also prove suitable, such as chitin and chitosan. Additional bioabsorbable materials are in intense development and it is expected that many of the new materials will also be applicable for forming a biodegradable plug 23 for a deflation valve in accordance with the present invention. Nontoxic inorganic salts having a low solubility (~0.00001 g/100 ml of stomach acid) may also prove useful for fabricating the plug 23 for the deflation valve 21.

While particular embodiments of the present invention have been illustrated and described, it would be obvious to those skilled in the art that various other changes and modifications can be made without departing from the spirit and scope of the invention. For example, the invention has been described as a self-deflating intragastric balloon. A key feature of the present invention that serves to distinguish the present intragastric balloon from prior art devices is the deflation valve affixed to the inflatable shell. The deflation valve may be used to enable the time-controlled non-invasive deflation of other implantable devices as well. It is therefore intended to cover in the appended claims all such changes and modifications that are within the scope of this invention.

What I claim is:

1. An implantable device comprising an inflatable elastomeric shell enclosing an interior chamber, said shell having a deflation hole therein, and a deflation valve affixed to said shell to occlude said deflation hole, the deflation valve comprising a biodegradable plug.

2. The implantable device of claim 1 wherein said device is an intragastric balloon.

3. The implantable device of claim 1 further comprising an insufflation valve affixed to said shell, said insufflation valve being operable for providing a leakproof seal between an insufflation catheter and said interior chamber.

4. The implantable device of claim 2 further comprising an insufflation valve affixed to said shell, said insufflation valve being operable for providing a leakproof seal between an insufflation catheter and said interior chamber.

* * * * *